United States Patent
Bodor et al.

(10) Patent No.: US 10,226,165 B2
(45) Date of Patent: Mar. 12, 2019

(54) OPTICALLY ADAPTIVE ENDOSCOPE

(71) Applicant: Integrated Medical Systems International, Inc., Birmingham, AL (US)

(72) Inventors: Peter Pal Bodor, Pembroke Pines, FL (US); Jurgen Zobel, Pembroke Pines, FL (US)

(73) Assignee: STERIS INSTRUMENT MANAGEMENT SERVICES, INC., Birmingham, AL (US)

(*) Notice: Subject to any disclaimer, the term of this patent is extended or adjusted under 35 U.S.C. 154(b) by 204 days.

(21) Appl. No.: 15/126,919

(22) PCT Filed: Mar. 18, 2015

(86) PCT No.: PCT/US2015/021205
§ 371 (c)(1),
(2) Date: Sep. 16, 2016

(87) PCT Pub. No.: WO2015/143015
PCT Pub. Date: Sep. 24, 2015

(65) Prior Publication Data
US 2017/0086657 A1   Mar. 30, 2017

Related U.S. Application Data

(60) Provisional application No. 61/954,884, filed on Mar. 18, 2014.

(51) Int. Cl.
*A62B 1/04* (2006.01)
*A61B 1/00* (2006.01)
(Continued)

(52) U.S. Cl.
CPC ...... *A61B 1/00188* (2013.01); *A61B 1/00009* (2013.01); *A61B 1/00096* (2013.01);
(Continued)

(58) Field of Classification Search
CPC .. A61B 3/102; A61B 3/1025; G01B 9/02038; G01B 9/02042; G01B 9/02091; G02B 19/0014; G02B 23/2407
(Continued)

(56) References Cited

U.S. PATENT DOCUMENTS

| 2008/0205833 A1* | 8/2008 | Fu | A61B 1/00096 385/117 |
| 2011/0137126 A1* | 6/2011 | French | A61B 1/00165 600/178 |

(Continued)

*Primary Examiner* — Gims S Philippe
(74) *Attorney, Agent, or Firm* — C. Brandon Browning; Maynard, Cooper & Gale, PC

(57) ABSTRACT

Optical systems for flexible and rigid endoscopes that have a low diffraction limit and small geometrical optical aberrations, the systems including an aperture stop where the diameter can be adjusted to select either higher resolution or higher depth of field. The optical systems can include a lens group either to focus on different object distances or on a fixed average object distance. The aperture stop can be adjusted to increase either depth of field or resolution dependent on the endoscopic and surgical situation. Simple symbols help the surgeon to adjust the aperture stop to these situations. The surgeon can either look around the body cavity with large depth of field but moderate overall resolution or focus on a small area with less depth of field but greater resolution. The balance between resolution and depth of field can be adjusted by an automatic image control. Fields in the image field are defined and software used in the camera controller analyzes the sharpness of the different fields. The center field is used to hold or define the sharpness of the image in the center field. Measurements of the sharpness in the peripheral fields define if more depth of field is needed or the resolution can be increased.

18 Claims, 18 Drawing Sheets

(51) Int. Cl.
*H04N 13/296* (2018.01)
*G02B 15/14* (2006.01)
*G02B 23/24* (2006.01)
*A61B 1/04* (2006.01)
*H04N 5/225* (2006.01)
*H04N 7/18* (2006.01)

(52) U.S. Cl.
CPC ............ *A61B 1/00114* (2013.01); *A61B 1/04* (2013.01); *G02B 15/14* (2013.01); *G02B 23/243* (2013.01); *G02B 23/2484* (2013.01); *H04N 5/2254* (2013.01); *H04N 7/183* (2013.01); *H04N 13/296* (2018.05); *H04N 2005/2255* (2013.01)

(58) Field of Classification Search
USPC .......... 348/65; 356/482; 600/101, 178, 328, 600/109; 385/117
See application file for complete search history.

(56) References Cited

U.S. PATENT DOCUMENTS

| | | | | |
|---|---|---|---|---|
| 2011/0228064 | A1* | 9/2011 | Sasaki | A61B 1/00096 348/65 |
| 2012/0265041 | A1* | 10/2012 | Yamaguchi | A61B 1/00004 600/328 |
| 2015/0015879 | A1* | 1/2015 | Papadopoulos | G02B 23/26 356/301 |
| 2015/0238071 | A1* | 8/2015 | Hua | A61B 1/07 600/109 |
| 2018/0084993 | A1* | 3/2018 | Buckland | A61B 3/1025 |

* cited by examiner

OPTICALLY ADAPTIVE ENDOSCOPE

CROSS REFERENCE TO RELATED APPLICATION

This application claims priority to U.S. Provisional Patent Application No. 61/954,884, entitled "Modular Endoscope System" and filed on Mar. 18, 2014 and PCT Application No: PCT/US15/21205, entitled "Optically Adaptive Endoscope" and filed on Mar. 18, 2015, which is incorporated herein by reference.

FIELD OF THE INVENTION

The invention relates to optical systems for flexible and rigid endoscopes which have a low diffraction limit and small geometrical optical aberrations.

BACKGROUND OF THE INVENTION

During the first half of the twentieth century, optical systems of endoscopes had low brightness and low resolution with large aberrations, especially at the periphery of the visual field. Antireflection coatings, multiple relay systems, the invention of the rod lens and improved objective designs increased brightness and resolution of optical systems in endoscopes. Recent increases in the numbers of pixels on video chips for HD and Ultra HD imaging and the improvement of video displays would seem to allow for improved resolution of the optical systems in endoscopes.

Two physical laws, however, limit the resolution of optical instruments. One physical law limiting the resolution of optical instruments is the diffraction limit. Based on the so-called diffraction limit of an optical system, the image of an object point imaged through an optical system cannot be a point. The image is a spot of a certain diameter in the image plane. This spot is called the airy disk. The size of the airy disk decreases with increasing aperture stop but cannot be improved by a more complicated or improved design.

The second limitation of optical instruments is geometrical optical aberrations. Geometrical optical aberrations cannot be avoided when the image of an extended object field is formed by an optical system like an endoscope. Every image of an object point is transferred in a spot caused by aberrations. This aberration spot increases with increasing aperture stop, but can be on the other side reduced by more complex optical designs.

These two limitations of resolution are not independent. The physical reality is that the airy disk and the aberration spot are overlaying one another in an image spot. The smallest possible image spot size is determined by the larger of either the airy disk or the aberration spot. Therefore, the smallest image spot is achieved when the airy disk and the aberration spot are about the same size. Even if the aberration spot size is extremely small, however, the image spot size can never be smaller than the airy disk.

As discussed herein, the image spot size is always considered the combined spot of the overlaid airy disk and the aberration spot. Resolution of an optical system such as endoscopes depends on the size of the image spot. The image spots overlay the pixels of the sensor in the image field. With the imaging scale of the overall optical system, the image spot can be adapted to the pixel size of a sensor like the retina of the human eye or like the chip of a video camera.

If the size of the image spot of the optical system is larger than the pixel size of the sensor, the resolution of the combined imaging system is limited by the spot size of the optical system and cannot meet the resolution of the sensor. If the size of the image spot of the optical system is equal to the pixel size of the sensor the resolution of the combined imaging system is now limited by the equal size of the imaging spot and the pixels of the sensor.

However, for optical systems like endoscopes with a fixed focus, only one object plane can be imaged to the corresponding image plane. Any object points outside of this object plane will have an image spot size larger than the size of the pixels on the sensor and will not appear sharp.

Only if the image spot size is significantly smaller than the pixel size of the sensor will the object points outside of this object plane have an image spot size smaller than the size of the pixels on the sensor and appear sharp. This is referred to as the depth of field (DOF) of optical systems. The extent of the DOF is dependent on both how much smaller the image spot is than the pixels on the sensor as well as the size of the aperture stop. The larger the aperture stop is, the smaller the DOF is for a given image spot size.

Flexible endoscopes have a physical stop as an aperture stop that is located in the objective at the tip of the endoscope. Rigid endoscopes, however, do not have a physical stop. For many rigid endoscopes, the aperture is by design limited by the inner diameter of the tubing of the optical system. Because of the low light transmission of rigid endoscopes this maximum aperture is desirable.

Variation of brightness in modern endoscopic systems is commonly adjusted by the integration time of the sensor elements of the video chip of the endoscopic camera and not by a variable aperture. Other applications use a tunable light source controlled by the feedback of the video camera to adjust the intensity of the light.

If a variable aperture stop is used, DOF and size of the airy disk can be modified. The electronically controlled brightness can be used corresponding with the optical brightness based on the stop size. The aperture stop formed by the inner diameter of the tubing has a correspondent image at the distal tip, the entrance pupil, and at the proximal end of the exit pupil. The exit pupil is located behind the proximal window.

Video chips with a higher resolution have more pixels on the same sensor area and therewith smaller pixels. To increase the resolution of an endoscope to meet the resolution of these video chips, the image spot size has to be decreased. This requires a better correction of the aberrations as well as a smaller airy disk. The better correction of aberrations is commonly achieved by a more complex optical system. The smaller airy disk can be achieved by increasing the aperture. The aperture of endoscopes can be increased with larger lens diameters and in case of rigid endoscopes additional with relay systems with a larger number of relay systems.

However, when the resolution of optical systems is increased, the DOF of these optical systems decreases. To come closer to the resolution offered by current high resolution imaging systems such as 1080p HD and Ultra HD (4K HD) can provide, the aperture of optical systems in endoscopes must be increased to a point where the DOF is reduced so much that such endoscopes cannot be used for an overview of an in-depth extended body cavity.

For endoscopes with such very small DOF, the setting of the focus is very important. Especially to inspect object fields at slightly different distances with high resolution, the focus has to be changed to the distance of each object field. Alternatively, the focus may be set to an appropriate distance, and the surgeon must attempt to find this distance and hold the endoscope steady. In contrary, to use such an endoscope with high resolution for the overview of an extended object field, the aperture stop has to be physically decreased to increase the DOF. The resulting loss in resolution has to be accepted.

This balance between high resolution and DOF is well known for other optical equipment, and measures are taken to overcome such problems. For example, in movies the director and camera man use different settings as expression of their art. Also professional photographers use variations of these settings of aperture, focus and DOF to compose their images.

To use endoscopes with such high resolution, a more modular endoscopic imaging system must be developed which can be adapted to various endoscopic applications and medical situations.

SUMMARY OF THE INVENTION

The ideas disclosed herein cover optical systems for endoscopes which have a low diffraction limit and small geometrical optical aberrations. Because of the low diffraction limit these endoscopes have a large aperture stop and therewith a small DOF but high resolution. Such endoscopes are only useful for some applications and situations. For many other applications, the endoscope system must be modular to adapt to various endoscopic situations and medical applications.

In a first variation of the disclosed ideas, the resulting large aperture stop in these optical systems with low diffraction limit and low geometrical aberrations can be decreased to increase the DOF when required by the application. However, a decrease in resolution has to be accepted. The corresponding decrease in brightness of the overall optical system can be compensated by an increase of the integration time of the sensor elements of the video chip. Alternatively, a tunable light source can be used. The tunable light source must be controlled by the feedback of the video camera to adjust the intensity of the light.

Flexible endoscopes have an objective system at the distal tip of the endoscope which creates an image on a flexible fiber image bundle or on a chip mounted at the distal tip. Such objective systems have a physical aperture stop built in the objective. If such an aperture stop is variable, the DOF can be increased when a reduced resolution is acceptable. Also, a lens or lens group in these objectives can be used to adjust the focus to object planes at different object distances.

Most rigid endoscopes do not have a physical aperture stop. However, the cross section of the light bundles through the aperture can be reduced at any of the correspondent images of the aperture, preferably at the exit pupil of the endoscope. This exit pupil is located behind the ocular and proximal window where the eye of an observer would be located. In the present disclosure, for rigid endoscopes with a large aperture and therewith low DOF, a physical aperture stop with variable opening is preferably placed at that exit pupil of the rigid endoscope.

It is preferred to locate this variable aperture stop in the tip of the endoscopic camera system where the exit pupil of the rigid endoscope overlays the entrance pupil of the objective of the endoscopic camera. That location is commonly referred to as the camera coupler and contains, behind a front window, the lens system needed to focus the endoscopic image on the chip. The camera coupler can be part of the camera housing containing the chip, or the coupler can be a separate unit.

Such variable aperture stops can be simply adjusted mechanically or electro-mechanically. With such aperture stops located in the camera coupler, the rigid endoscope itself has no moving parts or electric connections. In this first preferred embodiment no lens element is used to change the focus.

In a second preferred embodiment of the present disclosure, a variable aperture stop is combined with a movable lens element or lens group which is used to focus the imaging system on different object fields in different object distances. This change of focus position is especially important when the optical system of the endoscope is operated at the maximum aperture stop at maximal resolution but with the minimum DOF.

In flexible endoscopes with large apertures, a lens element or lens group in the tip of the endoscope must be movable to adjust the focus of the objective to object planes at different object distances. Rigid endoscopes commonly have no movable lens elements or lens groups and are focused on an object field at a median object distance. However, the focusing lens in the camera coupler is commonly movable to adjust the focus of the combined optical system of endoscope and camera coupler to object fields at different object distances in front of the rigid endoscope. The adjustable optical means in this second embodiment for rigid endoscopes, the variable aperture stop and the movable lens element or lens group can be combined in the camera coupler.

During an endoscopic procedure, the surgeon concentrates on the medical application and on a successful surgical procedure. He or she has little time to evaluate the endoscopic scenery or to adjust optical means to optimize the endoscopic image to any given situation. However, if the endoscopic image is not optimized, when the object distance or the position of the scope changes, loss in resolution of the object details or loss in DOF over the body cavity can compromise the outcome of the surgical procedure.

In the present disclosure, the settings of the adjustable optical means are related to situations in the endoscopic application and the surgeon only selects the medical situations whereby the adjustable optical means are changed accordingly and automatically. Simple symbols simplify the selection for the surgeon.

In this first type of embodiment, the surgeon can adjust the endoscopic imaging system to an overview setting. Corresponding to this setting, the aperture stop is closed mechanically or electro-mechanically to increase the DOF during the initial insertion of the endoscope in the body cavity and initial orientation within this body cavity. When the surgeon has identified the area he or she wants to operate on, the surgeon can switch to a second position or several different positions to provide increased resolution of the object field while limiting the ability to look around in the body cavity. In this position, the variable aperture stop is opened more, and the DOF is reduced. The surgeon may prefer several settings to adjust to different operating fields or different types of endoscopes.

In a second type of embodiment, the surgeon can also adjust the endoscopic imaging system to an overview setting. Corresponding to this setting, the aperture stop is closed and a movable lens element or lens group is set in a median focus position to extend the DOF during the initial insertion of the endoscope in the body cavity and orientation within this body cavity. The adjustment of the aperture stop and movable lens element or lens group can be done mechanically or electro-mechanically.

When the surgeon has identified the area on which he or she wants to operate, the surgeon can switch to a second position or several different positions providing an increased resolution of the object field and preferred at a closer object distance to the tip of the endoscope. In this position, the variable aperture stop is opened more by reduced DOF, and the imaging system is focused on an object field at a closer distance to the tip of the endoscope. This change increases the resolution by opening the aperture stop. With the closer distance between object field and endoscope, the magnification is higher and the overall resolution is increased. For this type of embodiment, the surgeon may prefer several settings to adjust to different operating fields or different types of endoscopes. The best focus can be found by the surgeon by varying the object distance to the area of interest the surgeon has selected.

In a third type of embodiment, the adjustment of the optical means of the endoscopic imaging system is controlled by electronic means. The surgeon only introduces the endoscope in the body cavity, moves the endoscope around to identify the position of the organs within the body cavity and finds the area of interest. After the surgeon has identified and is as close to the area of interest as he or she finds appropriate, the surgeon may start with the inspection and, if needed, the surgical procedure.

The electronic means, preferably located in the video controller, analyzes the image of the endoscope captured by the video camera and adjusts the optical means. The endoscopic image is analyzed in one or more areas in the center field of the endoscopic image. The image is also analyzed in several areas in the periphery of the endoscopic image.

The image analyzer produces numbers such as MTF values for a given frequency or contrast levels representing the sharpness of the image in each of the areas in the center field and peripheral field. Such software programs analyzing areas of images and measuring sharpness are well known in the art and are commercially available. This analysis is performed in real time and with the frequency of the image refresh rate.

During the procedure, the information about the sharpness in the center of the image field is used to adjust the movable lens element or lens group to focus on the object field. With more than one measured area in the center field of the endoscopic image, the numbers representing the sharpness of the images in the different areas may vary. This is the case when the multiple measured areas in the center field represent object fields at slightly different object distances. In this case, the movable lens element or lens group is adjusted so that the maximum of all numbers representing the sharpness of the multiple areas is minimized. This is the best compromise for the focus positions of these multiple areas.

The numbers the image analyzer produces, representing the sharpness of the images for the multiple areas in the peripheral field, are used to evaluate the need for more DOF. If the entire object field the endoscope oversees has an extended depth, the movable lens element or lens group may be adjusted to focus on the object distance represented by the object fields in the center area. However, the object fields displayed in the periphery of the endoscopic image will be out of focus. This means the numbers representing the sharpness of the images in the peripheral areas will be worth than those numbers representing the sharpness of the images in the central areas.

The electronic means will decrease the adjustable aperture stop and with that the DOF of the endoscope will increase. This will cause peripheral objects to appear sharper, and the numbers representing the sharpness of the images in the peripheral areas will decrease. However, the overall resolution of the endoscope will decrease because of the smaller aperture stop. Further, the numbers representing the sharpness of the images in the central areas will also decrease. The focus for the central area of the endoscopic image, however, will be held.

This process will continue until a balance between the numbers representing the sharpness of the images in the central areas and the numbers representing the sharpness of the images in the peripheral areas is achieved. This balance can mean the values are equal or, in case the center portion of the endoscopic image is more important, the process can be stopped if the peripheral image has improved to a predetermined ratio between the numbers representing the sharpness of the central areas and the sharpness of the peripheral areas.

If the object distances of the object fields observed in the central area and the object distances of the object fields observed in the peripheral area are in the same range, the numbers representing the sharpness of the images in the central areas and the numbers representing the sharpness of the images in the peripheral areas will be in the same range, and the aperture stop will not need to be closed. The electronic means is configured to select the best balance between the resolution and the DOF at any position the physician selects for the endoscope based on the surgical needs.

DETAILED DESCRIPTION

The first figures illustrate the optical and physical terms used in the description of the background of the invention. The successive figures show the different type of embodiments.

Figure 1:
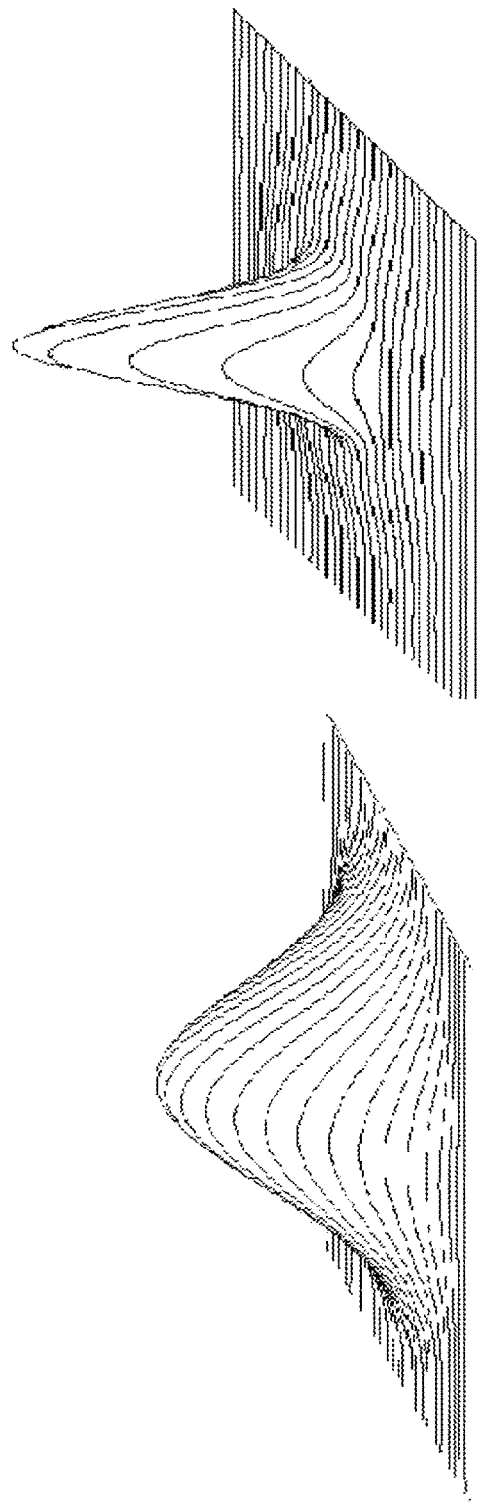
FIG. 1 depicts light distribution in an airy disk shown as a three-dimensional graph for low resolution and high resolution.

FIG. 1 depicts the light distribution in an airy disk. The depiction is shown as a three-dimensional graph of the light intensity distribution around the area of a theoretical image point. The left figure shows an airy disk for a small aperture with low resolution and the right figure shows a larger aperture with a higher resolution.

Figure 2:
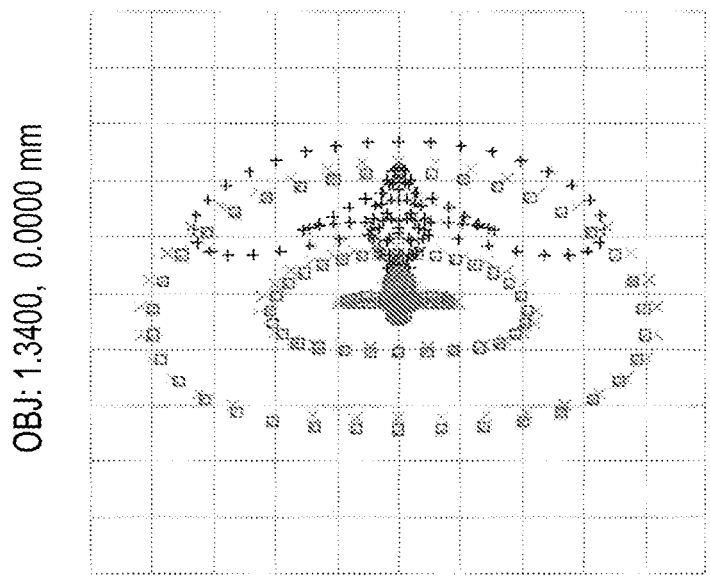
FIG. 2 depicts geometrical optical aberrations as a spot diagram for axial image point and off axial image point.
Figure 2:
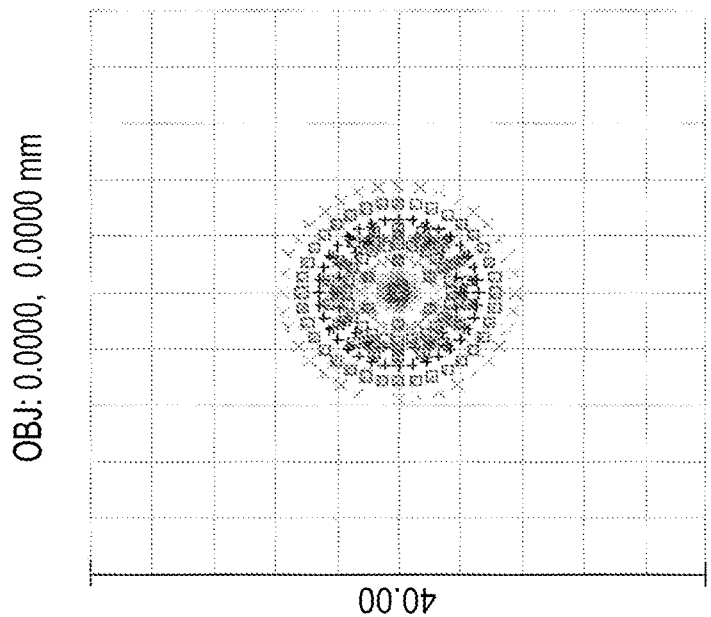

FIG. 2 depicts the geometrical optical aberrations of an optical system, wherein geometric optical aberrations are depicted as a spot diagram where a multitude of rays pass through the aperture of an optical system hitting the image plane. Each ray represents an equal portion of light intensity and forms a spot in the image plane. The size of the spot shows how much the aberrations are corrected. The left figure shows the aberrations of an axial image point. The right figure shows the aberrations of an off-axial image point with additional asymmetrical aberrations.

Figure 3:
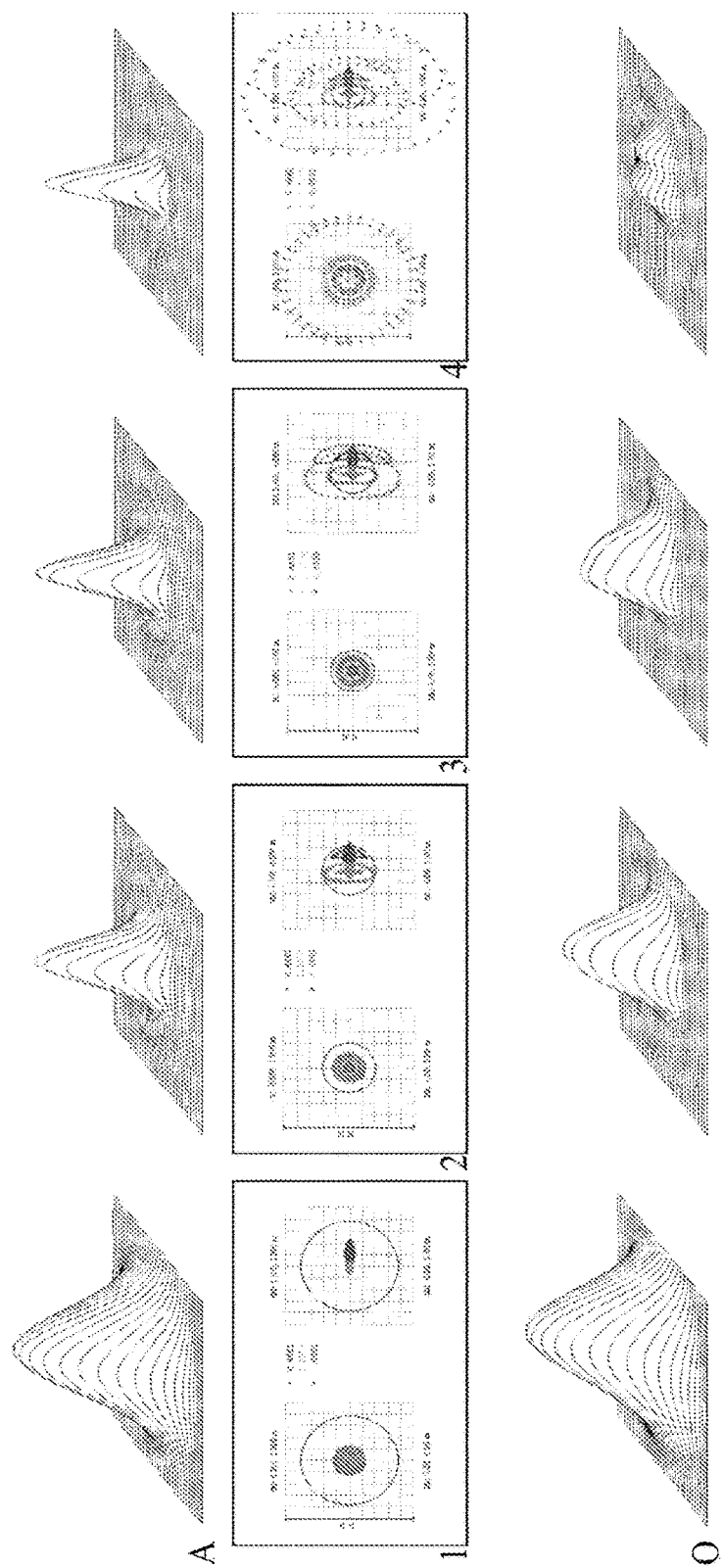
FIG. 3 depicts a comparison of airy disk and geometric optical aberrations for varying stop sizes for center and edge of image field.

FIG. 3 illustrates how the airy disk size and the geometrical optical aberrations influence one another. The center row of FIG. 3 depicts graphs 1 to 4 from left to right with an increasing aperture stop and the pure geometrical optical aberrations as a spot diagram. Each graph shows the geometrical optical aberrations for an axial point (left) and an off-axial point (right). Each graph also shows as an overlay to the geometrical optical aberration the size of the diffraction limited airy disk as a black circle. From graphs 1 to 4, the aperture stop increases, whereas the size of the diffraction limited airy disk decreases. However, with increasing aperture, the geometrical optical aberration worsen. The resulting real airy disk is now the diffraction limited airy disk deformed by the geometrical optical aberrations. For each of the four graphs the corresponding airy disk is shown. The top row "A" shows the corresponding airy disks for the corresponding axial points. The bottom row "0" shows the corresponding airy disks for the corresponding off-axial points.

In graph 1 of FIG. 3, the geometrical optical aberrations are small relative to the diffraction limited airy disk. Therefore, the airy disk is large (with a small aperture) but is minimally deformed by the geometrical optical aberrations. In graphs 2, 3 and 4 of FIG. 3, the geometrical optical aberrations increase and the diffraction limited airy disk decreases. Therefore, the airy disk gets smaller (and the aperture increases), but the geometrical optical aberrations deform the airy disk significantly. Further, a substantial amount of the light intensity is deviated in the area surrounding the diffraction limited airy disk. This series of graphs shows that the best image spot is achieved for an aperture where the diffraction limited airy disk overlaps the spot created by the geometrical optical aberrations.

Figure 4:
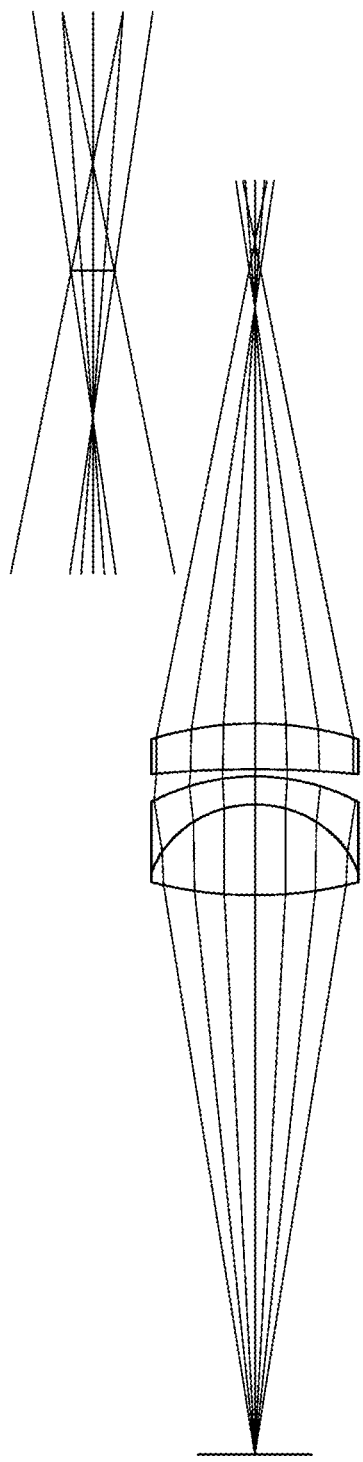
FIG. 4 is an illustration of the image spot size equal being equal to the pixel size of the sensor (rays in image spot magnified).
Figure 5:
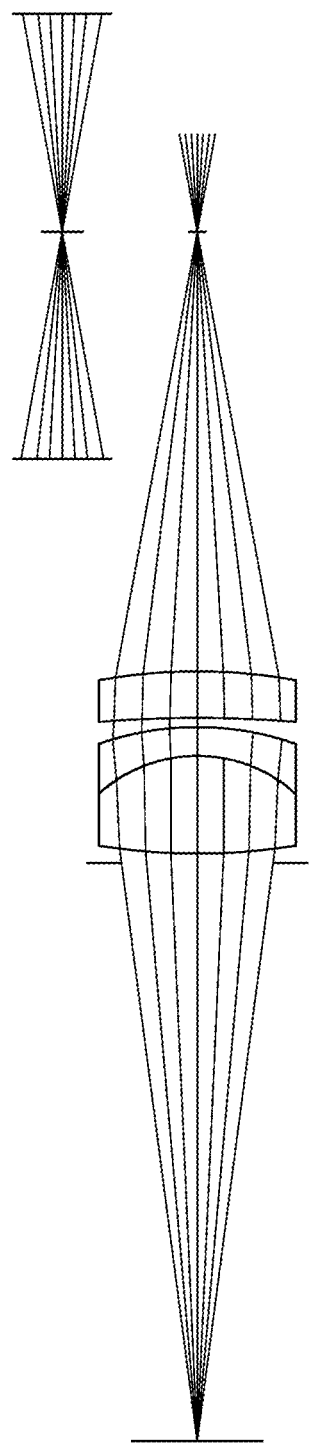
FIG. 5 is an illustration of the image spot size being smaller than the pixel size of the fixed sensor (rays in image spot magnified).

FIGS. 4 and 5 illustrate the resulting image spot relative to the size of a pixel on a video chip. FIG. 4 demonstrates that when the rays from a given object plane do not form a small spot size in the image plane, the resulting size of the image spot is equal to the size of the pixel on a video chip. In this case, every other object plane before or behind this given object plane cannot form a sharp image. The resulting size of the image spots for these object distances is larger than the size of the pixel on a video chip.

FIG. 5 shows that when the rays from a given object plane form a very small spot size in the image plane, the resulting size of the image spot is smaller than the size of the pixel on a video chip. In this case, other object planes before or behind this given object plane can still form a sharp image. The resulting size of the image spots is still smaller or equal to the size of the pixel on a video chip. The range of object distances where object planes may still form a sharp image on the pixel of the video chip is referred to as the DOF.

Figure 6:
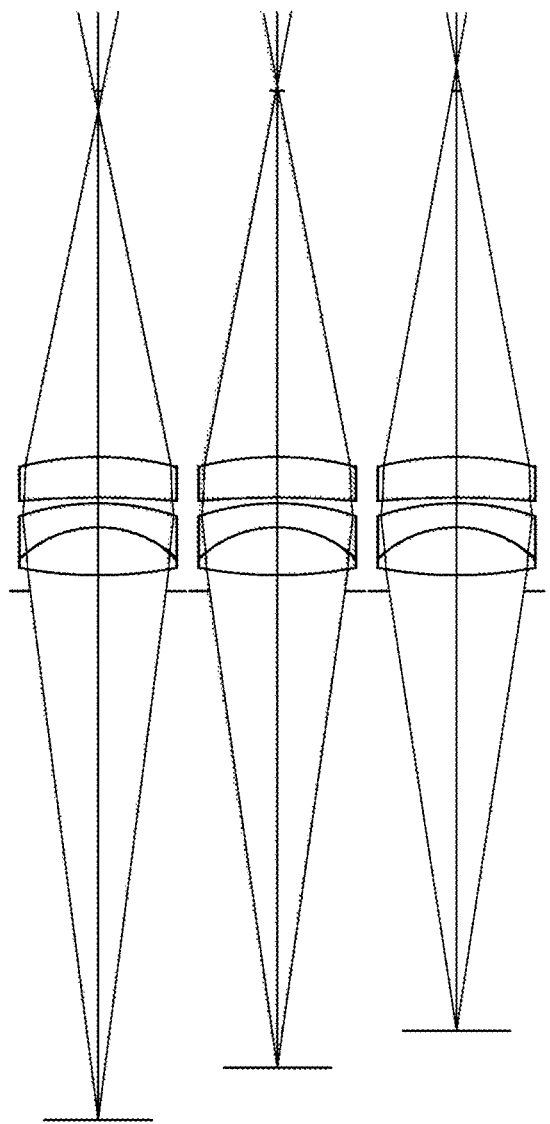
FIG. 6 is an illustration of different object positions where the image spot size is smaller than or equal to the pixel size of the fixed sensor.
Figure 7:
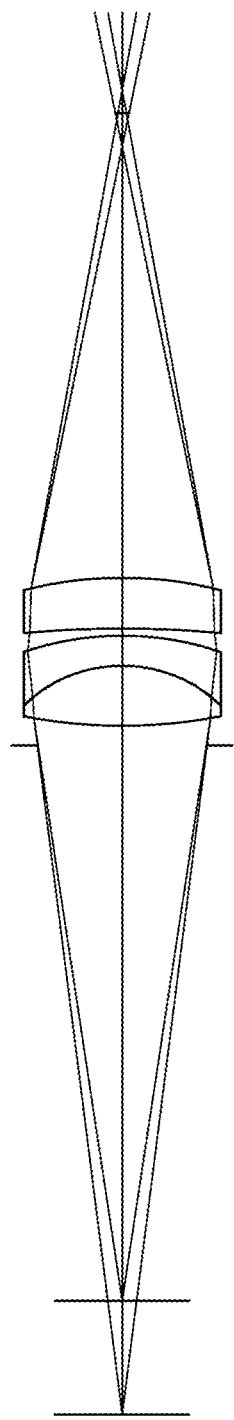
FIG. 7 is an illustration of extreme object positions where the image spot size is equal to the pixel size of the fixed sensor.

This is further depicted in FIGS. 6 through 9. FIG. 6 shows in three rows the same optical system where the image from different object distances is compared to the size of a pixel of a video chip located in a fixed image plane. The center row shows the object distance where the image spot is minimized in the image plane. The top row shows an object distance farther away from the optical system where the image spot is as large as the pixel of the video chip. The bottom row shows an object distance closer to the optical system where the image spot is also just as big as the pixel of the video chip. The range between these two extreme object distances is the DOF. FIG. 7 shows the two extreme object distances forming the DOF overlapped in one figure.

Figure 8:
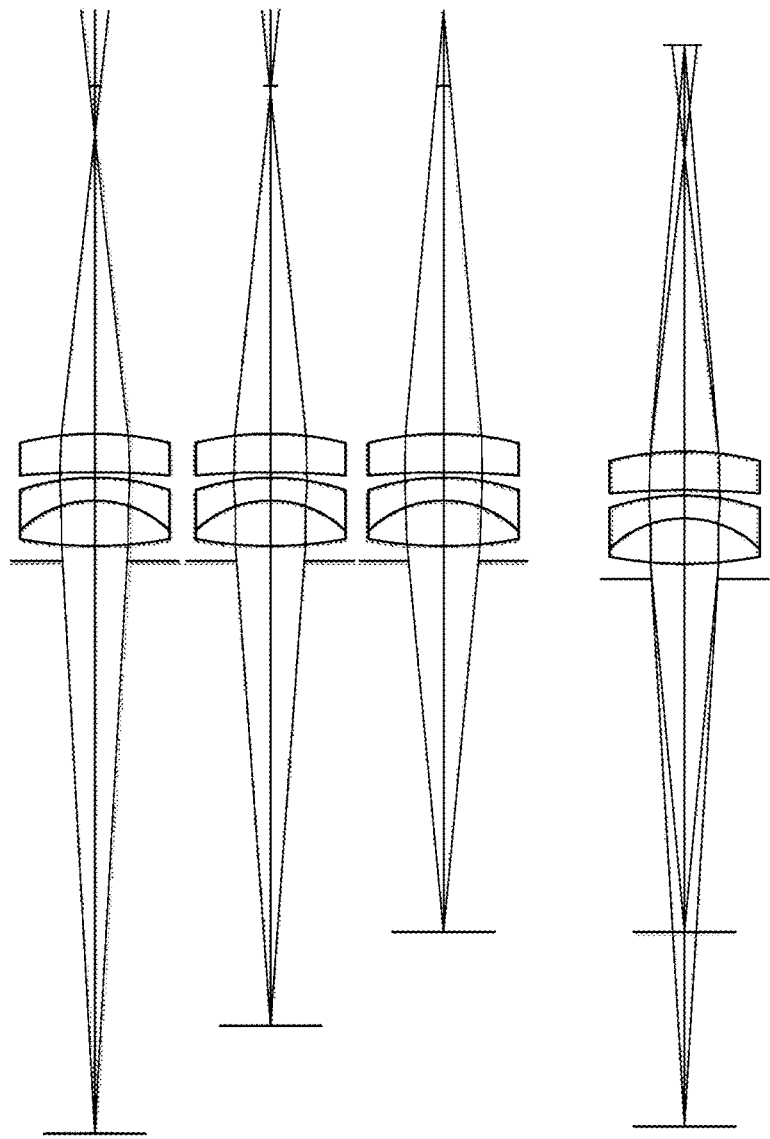
FIG. 8 is an illustration of how smaller aperture stop relates to an extended object area still sharp on the sensor (large DOF).
Figure 9:
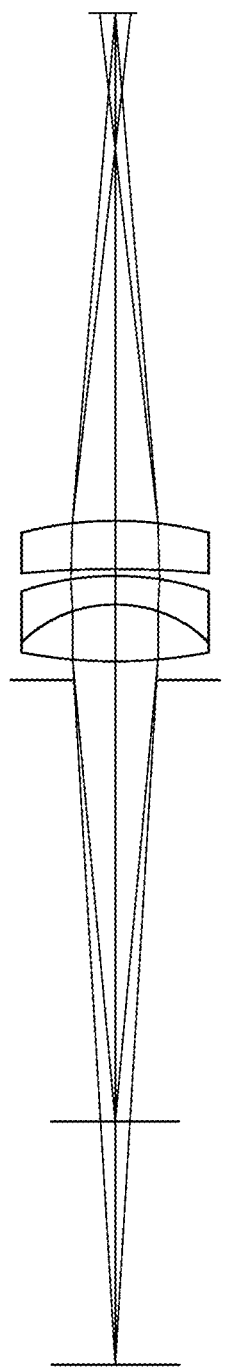
FIG. 9 is an illustration of an example of extreme object positions for smaller aperture size (large DOF).

FIG. 8 shows the same optical system with a smaller aperture stop. FIG. 8 shows in three rows the same optical system with a smaller aperture stop, where the image from different object distances is compared to the size of a pixel of a video chip located in a fixed image plane. The center row again shows the object distance where the image spot is minimized in the image plane. The top row of FIG. 8 shows an object distance farther away from the optical system where the image spot is as big as the pixel of the video chip. The bottom row shows an object distance closer to the optical system where the image spot is also as big as the pixel of the video chip. The range between these two extreme object distances is larger than in FIG. 6, which results in a larger DOF. FIG. 9 shows the two extreme object distances forming the DOF overlapped in one figure.

Figure 10:
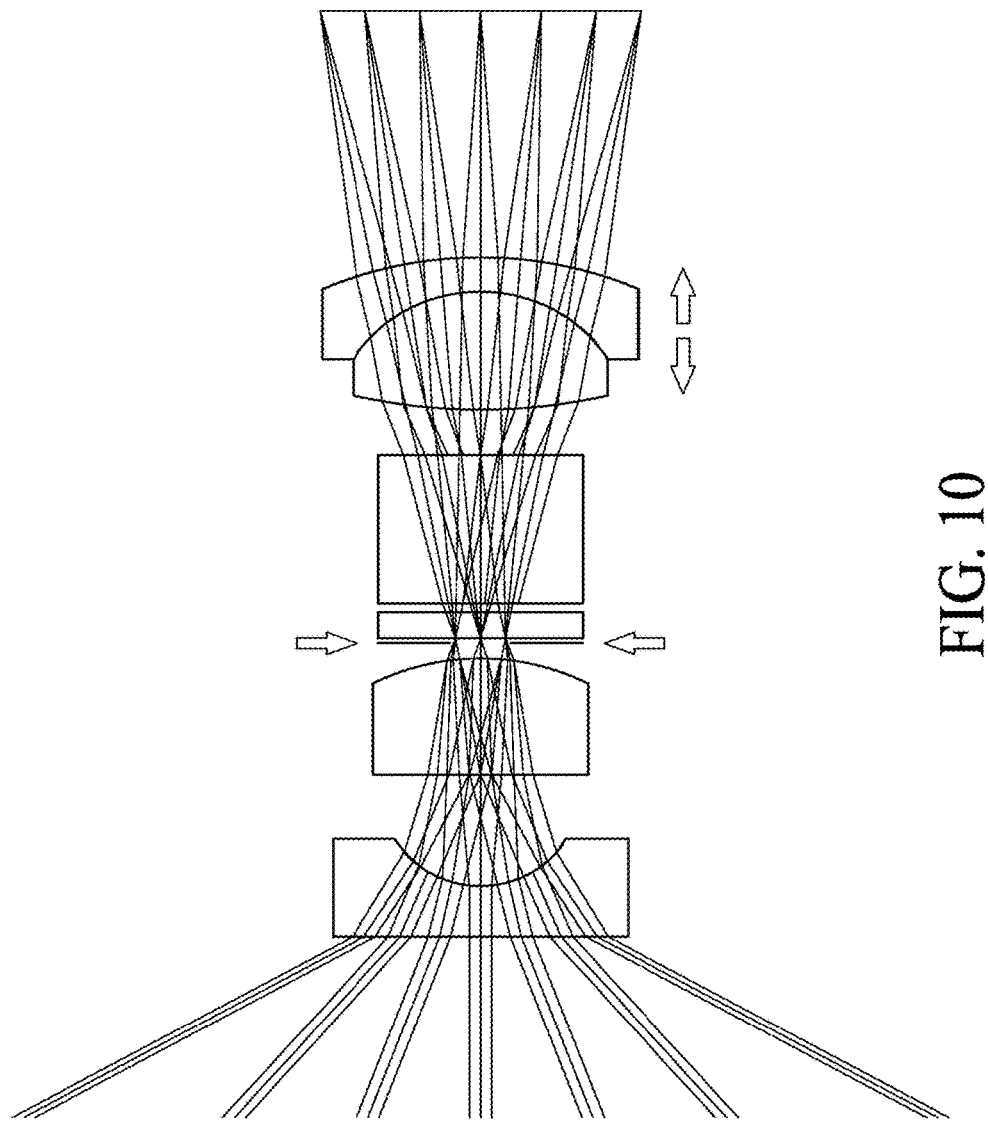
FIG. 10 is an illustration of an exemplary objective system for flexible endoscope with lens system aperture stop and fiber image bundle or video chip.

FIG. 10 depicts an exemplary optical system for a flexible endoscope. On the right side in the image plane is an image sensor. This image sensor can be either a video chip or a fiber image bundle. The pixel size of the image sensor and the size of the aperture stop in the middle of the objective limits the DOF. The last lens can be movable to adjust the center of the object field to enable the optimal focus.

Figure 11:
FIG. 11 is an illustration of an exemplary last relay of an endoscope with an ocular, proximal window and exit pupil.

FIG. 11 depicts the last relay of an endoscope and an ocular with the proximal window. Rays are shown for the axial and peripheral points and the ray bundle going through the exit pupil. The exit pupil is located behind the proximal window where the eye of the observer is located.

Figure 12:
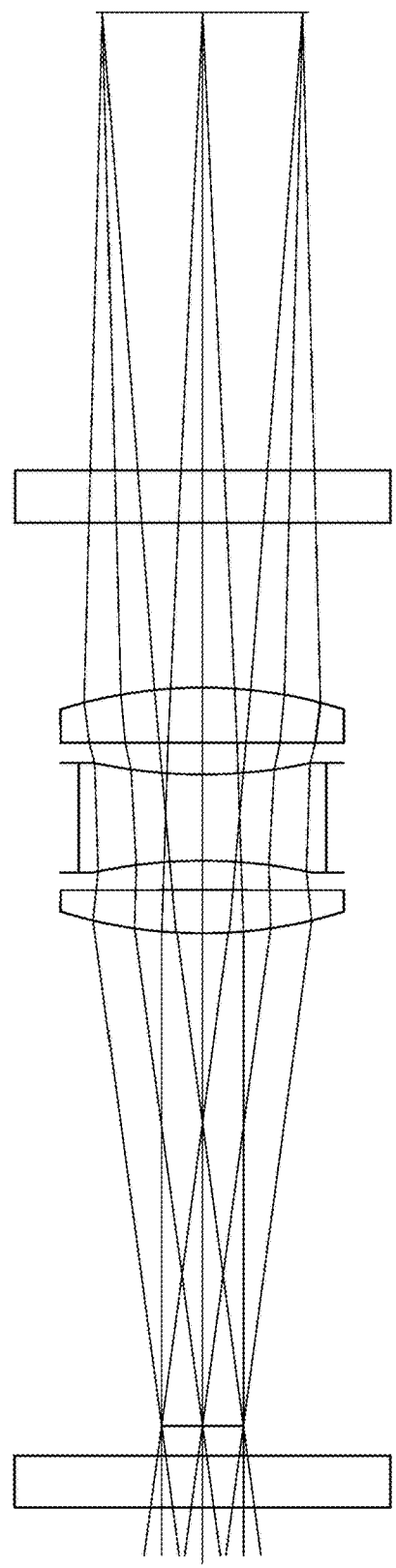
FIG. 12 is an illustration of a camera coupler with front and back windows.

FIG. 12 shows the lens system of a camera coupler with a front and back window. The ray bundle for the axial and peripheral points go through the entrance pupil of the camera coupler. On the right side is the image field where the video chip is located.

Figure 13:
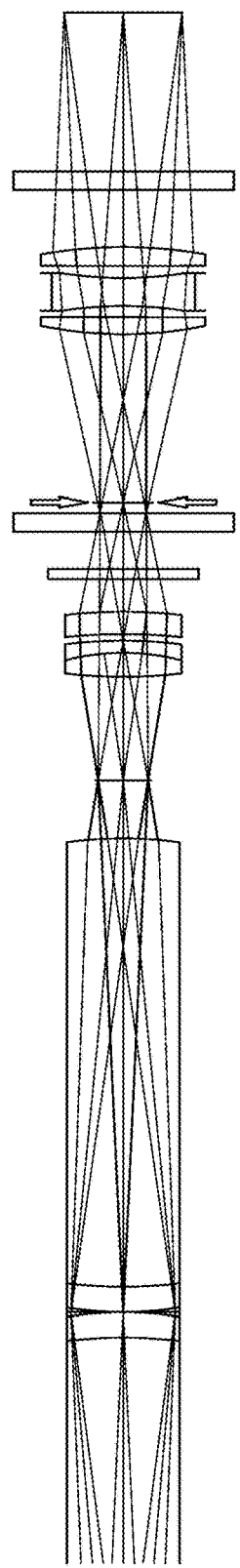
FIG. 13 is an illustration of an exemplary last relay of endoscope with ocular, proximal window and exit pupil adapted to coupler & camera.

In FIG. 13, the last relay from FIG. 11 is overlaid to the camera coupler from FIG. 12. The exit pupil of the endoscope falls exactly on the entrance pupil of the camera coupler. Therefore, the diameter of the aperture stop of the rigid endoscope can be modified by modifying the diameter of the entrance pupil of the camera coupler. The two arrows indicate this position of the aperture stop.

Figure 14:
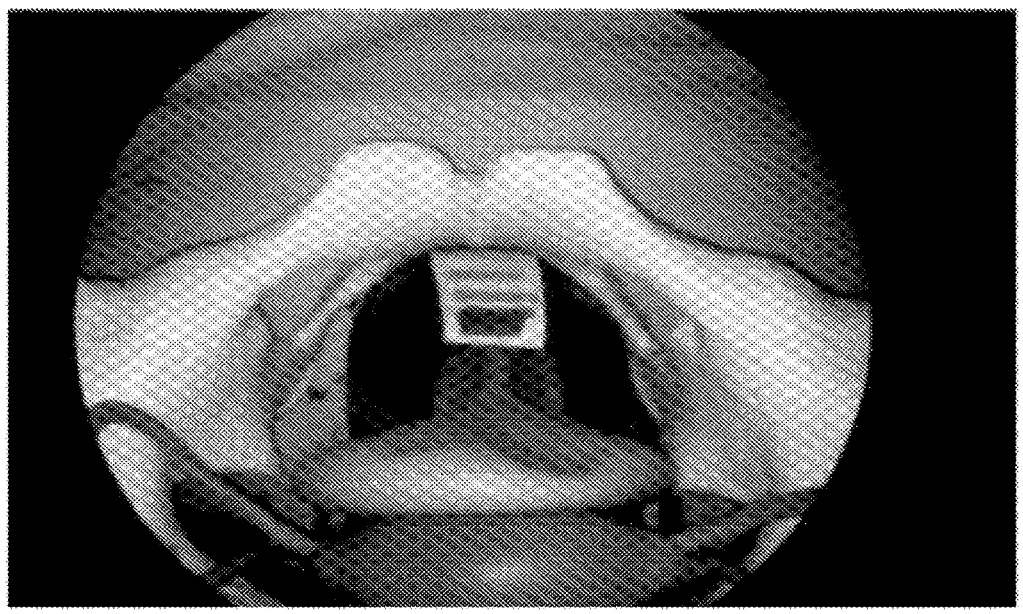
FIG. 14 is a photograph of an endoscopic image from an anatomic model showing the extended depth in the object field.

FIG. 14 shows a photograph of an endoscopic picture of the abdomen in an anatomic model. The depth in the body cavity and the different distances of the organs and bones demonstrate the need for a large DOF in the overview position.

Figure 15:
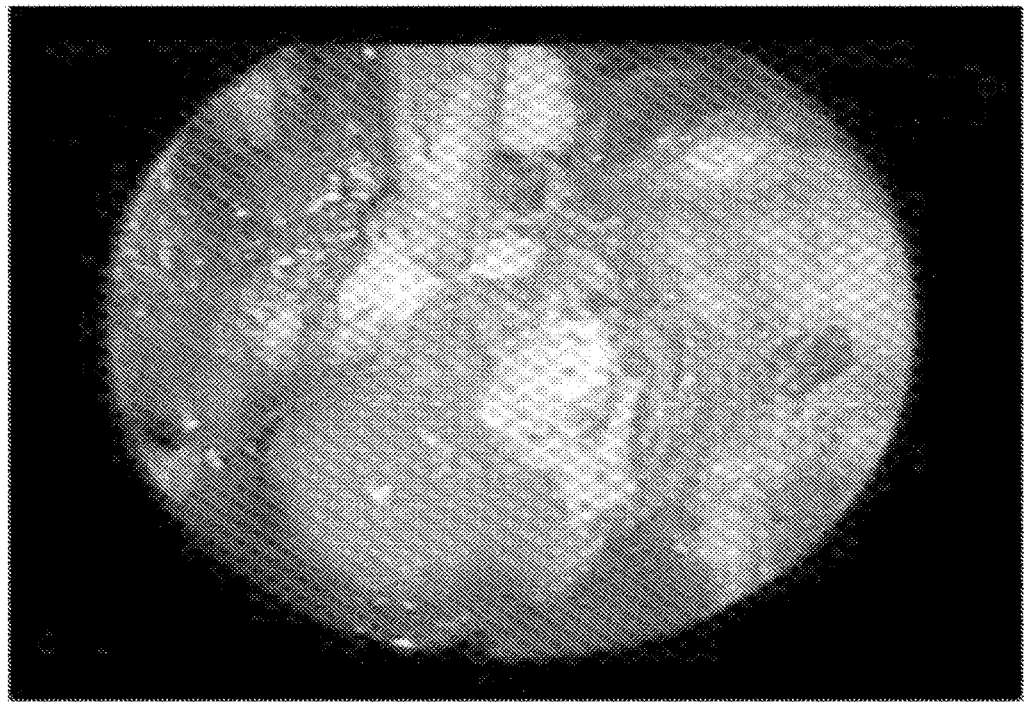
FIG. 15 is a photograph of an endoscopic image showing an instrument doing surgery on an organ in the abdomen.

FIG. 15, in contrast to FIG. 14, shows an endoscopic photograph of an instrument during surgery on an organ. The blurry image in FIG. 15 demonstrates the need to have proper focus and high resolution around the central area. An extended DOF is not necessary.

Figure 16:
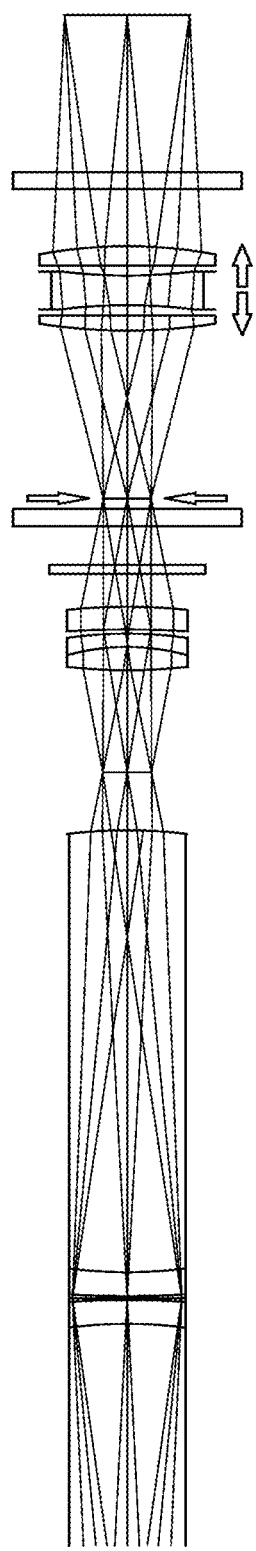
FIG. 16 is an illustration of an exemplary last relay of an endoscope with an ocular, proximal window and exit pupil that is coupled to a variable aperture stop and a focusable lens system.

FIG. 16, like FIG. 13, depicts the last relay from FIG. 11 overlaid to the camera coupler from FIG. 12. The exit pupil of the endoscope falls exactly on the entrance pupil of the camera coupler. The diameter of the aperture stop of the rigid endoscope can be modified by modifying the diameter of the entrance pupil of the camera coupler. In addition, the coupler lens can be moved to focus object fields from different object distances in front of the rigid endoscope on the video chip. The two vertical arrows indicate this position of the aperture stop and the two horizontal arrows show the axial movement of the coupler lenses to adjust the focus.

Figure 17:
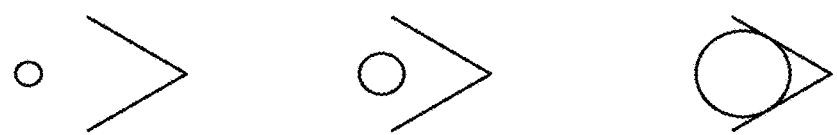
FIG. 17 is an illustration of sample for a simple symbolic for the camera setting including, from left to right, overview, middle position, and close-up position.

FIG. 17 illustrates simple symbols designed to advise the surgeon to select appropriate settings for different endoscopic and surgical situations. The circle in FIG. 17 represents the object in center and the angled lines represent the whole field of view. The left symbol indicates an overview position where the center object is of minor importance but DOF is needed to look around the whole field of view. The right symbol indicates the center object fills the whole field of view where DOF is not important but high resolution is required.

Figure 18:
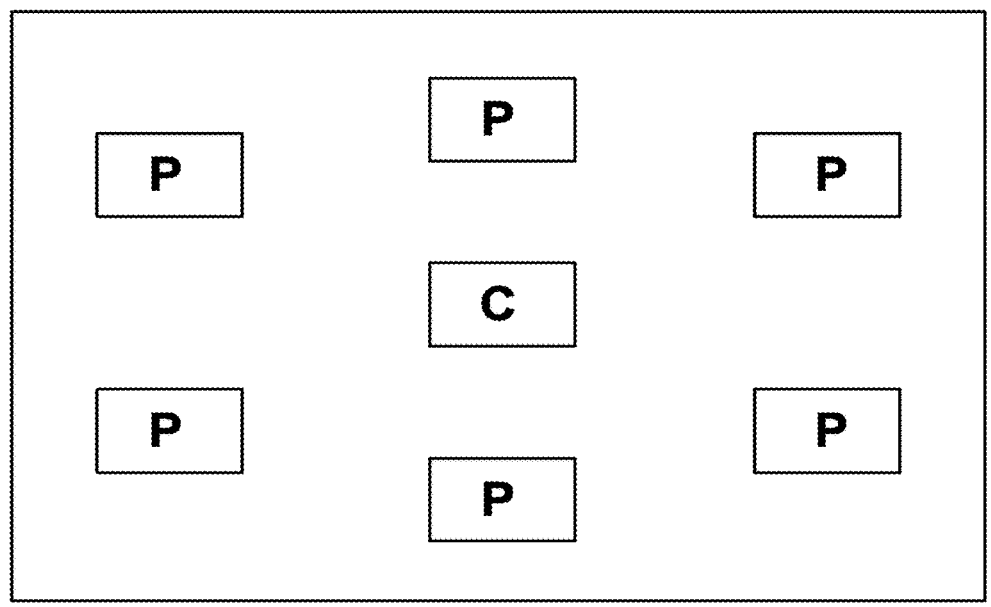
FIG. 18 is an illustration of fields in image space to detect sharpness in center (C) and peripheral fields (P) to compare to the center field.

FIG. 18 illustrates the image field represented by the endoscopic image where one or more fields in the image area are used to measure the relative sharpness in these fields. The left image shows a preferred embodiment where only one field in the center (C) of the image is used to measure the sharpness in this image area. The focus is then adjusted with a lens group in the endoscope or in the coupler to keep the best focus. The DOF is preselected by the aperture stop dependent if the endoscopic and surgical situation requires a full overview of the body cavity or best resolution of the center field.

The right picture in FIG. 18 shows another preferred embodiment where a field in the center (C) of the image is surrounded by peripheral fields (P). The center field is used to measure the sharpness of the center image area. The focus is then adjusted with a lens group in the endoscope or in the coupler to optimize the focus. The peripheral fields are also used to measure the sharpness in these peripheral image areas. The information from the peripheral areas is then used to determine if a larger DOF is needed. The measured sharpness in these peripheral areas is compared to the sharpness in the center area. If the sharpness measured in the peripheral areas is worse than in the central area more DOF for this endoscopic situation is needed.

The electronic means in the camera is used to close the aperture stop automatically. The focus will be held steadily on the object distance of the object in the center field. However, the sharpness in the center field will decrease because of decreasing resolution. However, the DOF is increased concurrently with an increase in the sharpness of the peripheral fields.

When the aperture stop continuously decreases, the sharpness in the center will decrease, but the sharpness in the peripheral fields will increase. This process continues until a balance between a relatively sharp center field and relatively sharp peripheral fields is achieved. At such a point, all fields in the image field will be of approximately the same sharpness, thereby allowing the surgeon to look around in the image field. If the sharpness measured in the peripheral areas is of the same sharpness as the sharpness in the central area, no increased DOF for this endoscopic situation is needed.

The electronic means in the camera is used to open automatically the aperture stop. The focus may be controlled automatically by the central field. The sharpness in the center field will increase because of increased resolution. However, this will cause the DOF to decrease. If the peripheral fields are objects at different object distances than the object in the central field, the sharpness in the peripheral fields will decrease. The increase in resolution of the center field will increase until the peripheral fields will become less sharp than the center field. This continues until a balance between a sharp center field and equally sharp peripheral fields is achieved. All fields in the image field are again of same sharpness but the surgeon looks this time on a small field area with higher resolution because no additional DOF is needed.

It should be emphasized that the embodiments described herein are exemplary, and various changes and modifications to the embodiments illustrated herein are possible.

What is claimed is:

1. An imaging system for an endoscope with an optical system that has a low diffraction limit and small geometrical optical aberrations, the imaging system comprising,
   an endoscopic video system including a video sensor and a control unit configured for processing an optical image wherein a cross section of an aperture of an optical system is adjustable and the optical system is configured for focusing on different object distances by means of a movable lens element or a lens group for optimizing the imaging system for various endoscopic applications,
   wherein the control unit is configured for processing the optical image using electronic means to analyze the optical image of the endoscope captured by a video camera in several peripheral areas of the optical image to determine the sharpness of the optical image at the periphery and to reduce the aperture of the optical system until a balance between the sharpness of the center field and the sharpness of the peripheral fields is achieved.

2. The imaging system according to claim 1, wherein the endoscope is a flexible endoscope configured for enabling adjustment of the aperture in an objective in a tip of the endoscope and for enabling adjustment of the lens element or the lens group in the objective.

3. The imaging system according to claim 2, wherein the endoscopic video system including the video sensor is located at a tip of the endoscope behind the objective and includes an electric cable configured for relaying the a video image to a proximal end of the endoscope outside of a body cavity by transferring the video image to the control unit of the imaging system.

4. The imaging system according to claim 1, wherein the optical system of the endoscope is a rigid endoscope including an objective system, a relay system and an ocular, wherein the endoscopic video system is located at a proximal end of the optical system with an endoscopic camera coupler including a lens system, a camera head including the video sensor and the control unit wherein the cross section of the aperture of the optical system is adjustable in the camera coupler and the movable lens element or the lens group in the camera coupler is adjustable.

5. The imaging system according to claim 1, wherein the control unit includes electronic means configured for analyzing the image of the endoscope captured by the video sensor in a center area of the image for determining the sharpness of the image and for adjusting the lens element or the lens group to increase the sharpness of the image in the center field.

6. The imaging system according to claim 1, wherein the cross section of the aperture of the optical system is adjustable by a mechanical means and the lens element or the lens group is adjustable by another mechanical means.

7. The imaging system according to claim 6, wherein the mechanical means for reducing the aperture and the mechanical means for moving the lens element or the lens group are coupled with a mechanical indicator labeled with symbols relating to surgical situations.

8. The imaging system according to claim 1, wherein the cross section of the aperture of the optical system is adjustable by electro-mechanical means and the lens element or the lens group is adjustable by another electro-mechanical means.

9. The imaging system according to claim 1, wherein the cross section of the aperture of the optical system is adjustable by mechanical means and the lens element or the lens group is in a fixed position.

10. The imaging system according to claim 9, wherein the mechanical means for reducing the aperture is coupled with a mechanical indicator labeled with symbols relating to surgical situations.

11. The imaging system according to claim 1, wherein a model number of the endoscope can be typed in the control unit to set a minimum diameter and a maximum diameter for the aperture and to set a focus range for the lens element or lens group for the endoscope.

12. The imaging system according to claim 1, further comprising a fiber image bundle that is configured for relaying the optical image to a proximal end of the endoscope wherein the video sensor is located at the proximal end of the endoscope outside of a body cavity.

13. The imaging system according to claim 1, wherein the electro-mechanical means is configured for analyzing the optical image of the endoscope using one or more separate fields in a center area of the image to determine the sharpness of the optical image in each field and for adjusting the lens element or the lens group to increase the sharpness of the optical image of all center fields.

14. The imaging system according to claim 1, wherein the electro-mechanical means is configured for calculating a Modulation Transfer Function for a given frequency for an image field in a center of the optical image or to calculate the Modulation Transfer Function for a given frequency for all image fields in the center and periphery of the endoscopic image to determine the sharpness of each measured field.

15. The imaging system according to claim 1, wherein the electro-mechanical means is configured for calculating a contrast level for an image field in a center of the optical image or to calculate contrast levels for all image fields in the center and a periphery of the optical image to determine the sharpness of each measured field.

16. The imaging system according to claim 1, wherein the optical system is a flexible stereo endoscope and the mechanical means for reducing the aperture and the means for moving the lens element or the lens group are coupled together for the left and right channel.

17. The imaging system according to claim 1, wherein the optical system is a rigid stereo endoscope and the means for reducing the aperture stop and the means for moving the lens element or the lens group are coupled together for the left and right channel.

18. The imaging system according to claim 1, wherein the endoscopic video system including the video sensor is located at a tip of the endoscope behind an objective and includes an electric cable configured for relaying the a video image to a proximal end of the endoscope outside of a body cavity by transferring the video image to the control unit of the imaging system.

* * * * *